(12) United States Patent
Collier et al.

(10) Patent No.: US 7,858,762 B2
(45) Date of Patent: Dec. 28, 2010

(54) **PHOSPHATE LIMITED INDUCIBLE PROMOTER AND A *BACILLUS* EXPRESSION SYSTEM**

(75) Inventors: Katherine D Collier, Redwood City, CA (US); Edwin Lee, San Francisco, CA (US); Nicholas Leiva, San Francisco, CA (US); Thomas B Morrison, Winchester, MA (US); Volker Schellenberger, Palo Alto, CA (US); Olga V Selifonova, Plymouth, MN (US); Adam C Kean, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 1152 days.

(21) Appl. No.: 10/483,842

(22) PCT Filed: Jul. 26, 2002

(86) PCT No.: PCT/US02/23829

§ 371 (c)(1),
(2), (4) Date: Jun. 29, 2004

(87) PCT Pub. No.: WO03/054140

PCT Pub. Date: Jul. 3, 2003

(65) Prior Publication Data

US 2005/0079571 A1    Apr. 14, 2005

Related U.S. Application Data

(60) Provisional application No. 60/308,922, filed on Jul. 30, 2001.

(51) Int. Cl.
*C07H 21/02* (2006.01)
*C07H 21/04* (2006.01)
*A61K 39/38* (2006.01)
*A61K 39/07* (2006.01)

(52) U.S. Cl. ............... 536/23.1; 424/184.1; 424/246.1; 536/23.7

(58) Field of Classification Search .............. 424/184.1, 424/93.46, 93.462; 530/300
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,965,188 A | 10/1990 | Mullis et al. | 435/6 |
| 5,304,472 A | 4/1994 | Bass et al. | 435/69.1 |
| 5,411,873 A | 5/1995 | Adams et al. | 435/69.1 |
| 5,789,199 A | 8/1998 | Joly et al. | 435/69.1 |
| 5,939,315 A | 8/1999 | Adams et al. | 435/320.1 |
| 6,175,060 B1 | 1/2001 | Lefebvre et al. | 800/295 |

OTHER PUBLICATIONS

Qi et al (Journal of Bacteriology, Apr. 1997, p. 2534-2539).*
Qi et al (Molecular Microbiology, 1998, 28(6); 1187-1197).*
Takemaru et al (Microbiology, Aug. 1996; 142(Pt 8):2017-20) (Abstract only).*
McGuinnes et al. (Mol. Microbiol. 7: 505-514, Feb. 1993).*
McGuinnes et al. (Lancet 337: 514-517, Mar. 1991).*
Bowie et al (Science, 1990, 257:1306-1310).*
Hale & Marham, *The Harper Collins Dictionary of Biology*, Harper Perennial, NY, 1991.
International Search Report for PCT/US02/23829 filed Jul. 26, 2002.
Liu et al., Sites Internal to the Coding Regions of *phoA* and *pstS* Bind PhoP and are Required for Full Promoter Activity, Molecular Biology, vol. 28, No. 1, pp. 119-130 (1998).
Qi et al., "PhoP~P and RNA Polymerase $\sigma^A$ Holoenzyme are Sufficient for Transcription of Pho Regulon Promoters in *Bacillus subtilis*: PhoP~P Activator Sites Within the Coding Region Stimulate Transcription In Vitro," Molecular Microbiology, vol. 28, No. 6, pp. 1187-1197 (1998).
Singleton et al., *Dictionary of Microbiology and Molecular Biology*, 2nd ed., John Wiley & Sons, New York, 1994.

* cited by examiner

*Primary Examiner*—Vanessa L. Ford
(74) *Attorney, Agent, or Firm*—Danisco US Inc.

(57) ABSTRACT

An evolvable production strain of *B. subtilis* exhibiting continuous or high level expression during protein evolution is described. An evolved *Bacillus subtilis* pstS promoter facilitates screening and production of secreted proteins.

7 Claims, 9 Drawing Sheets

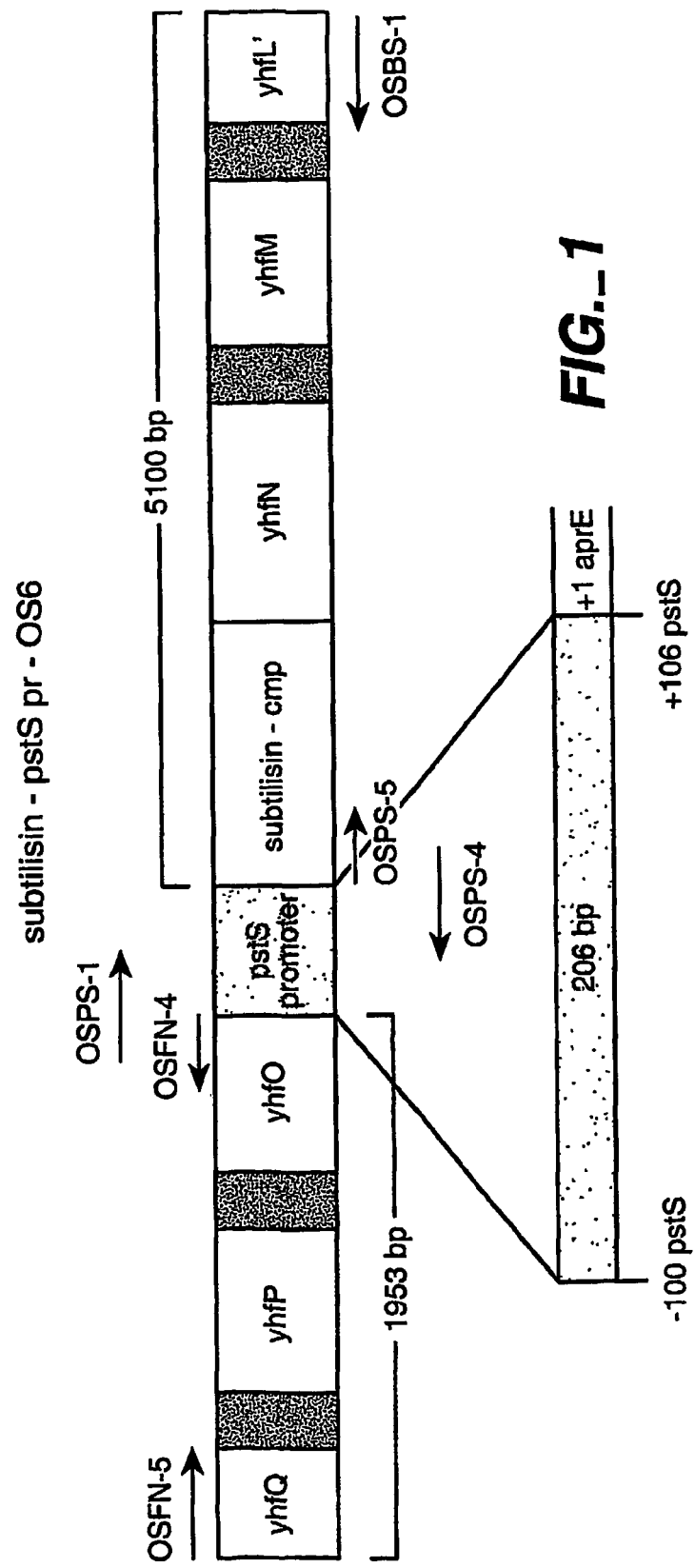
FIG._1

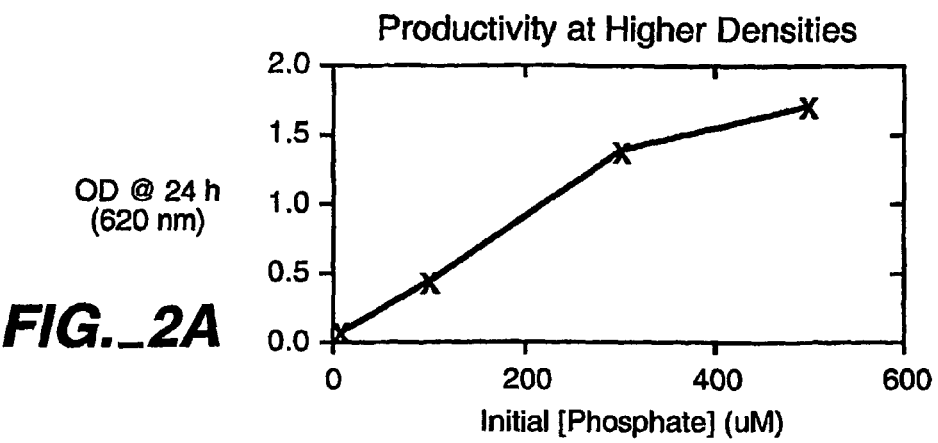
FIG._2A
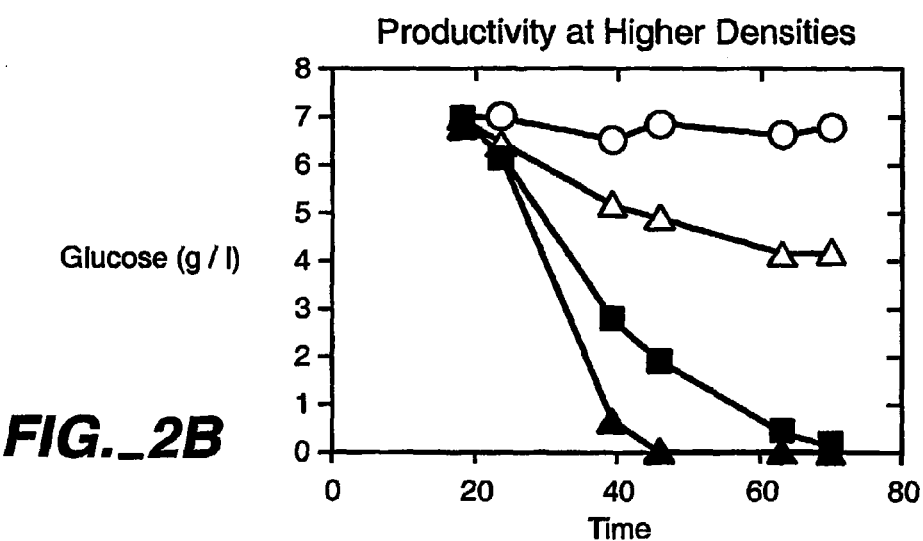
FIG._2B
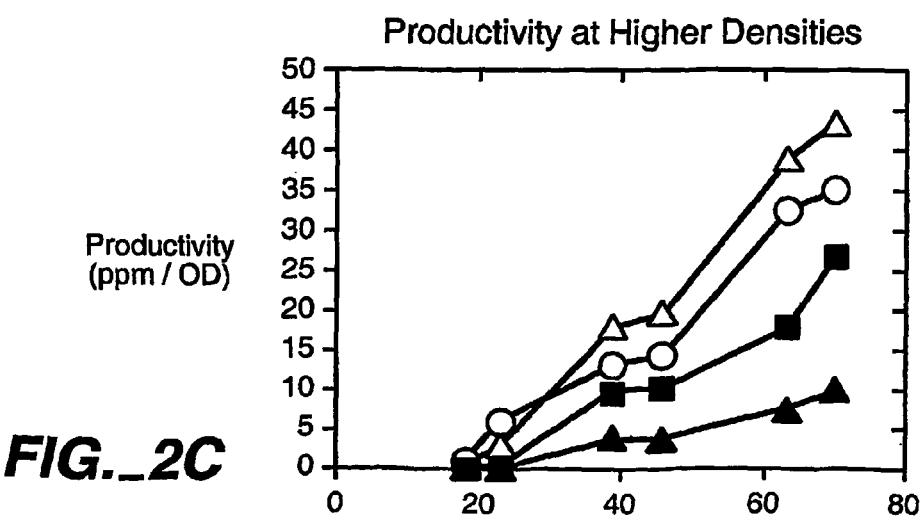
FIG._2C

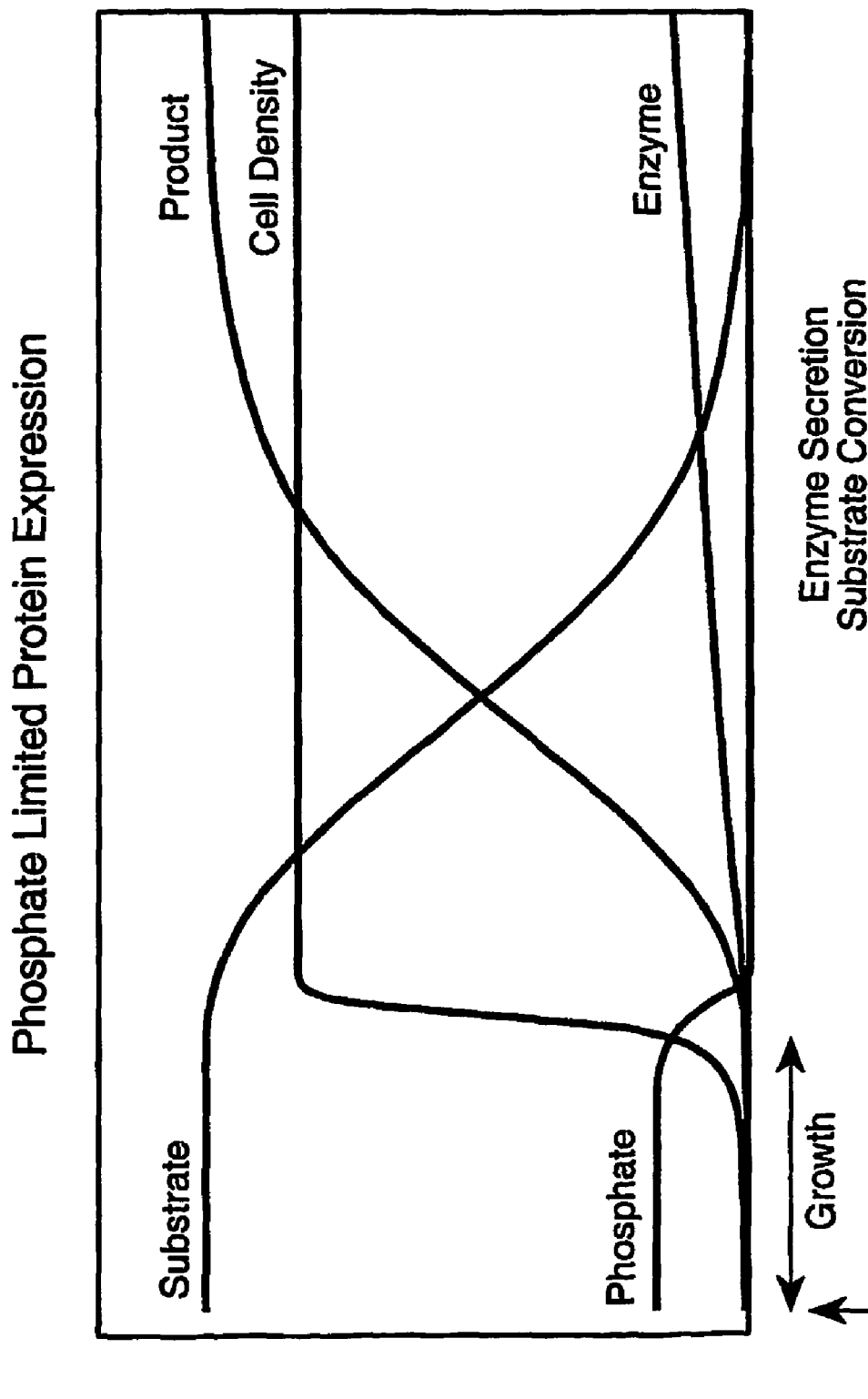
FIG._3

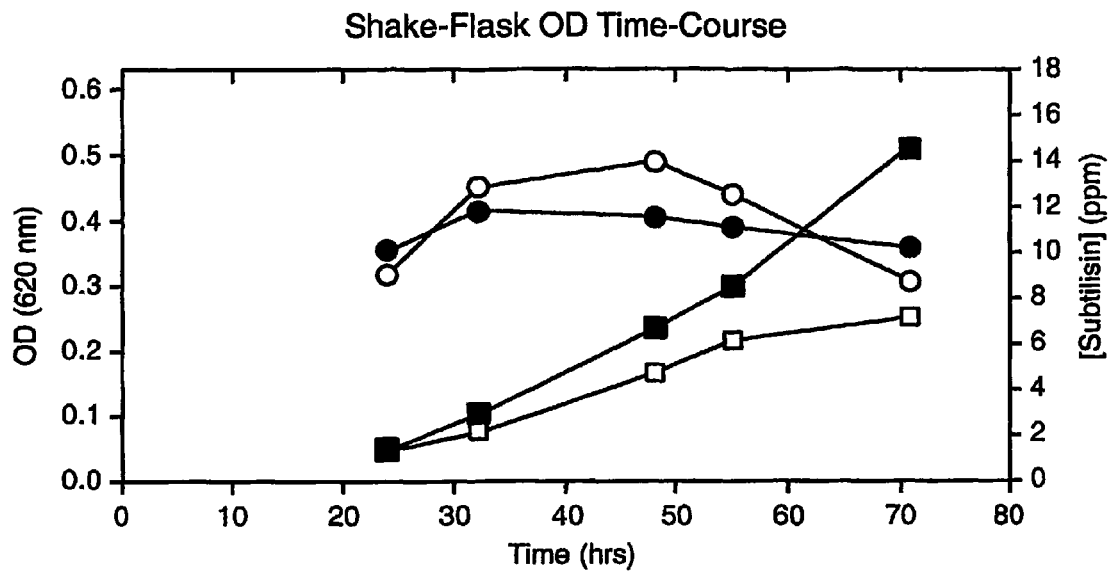
FIG._4A
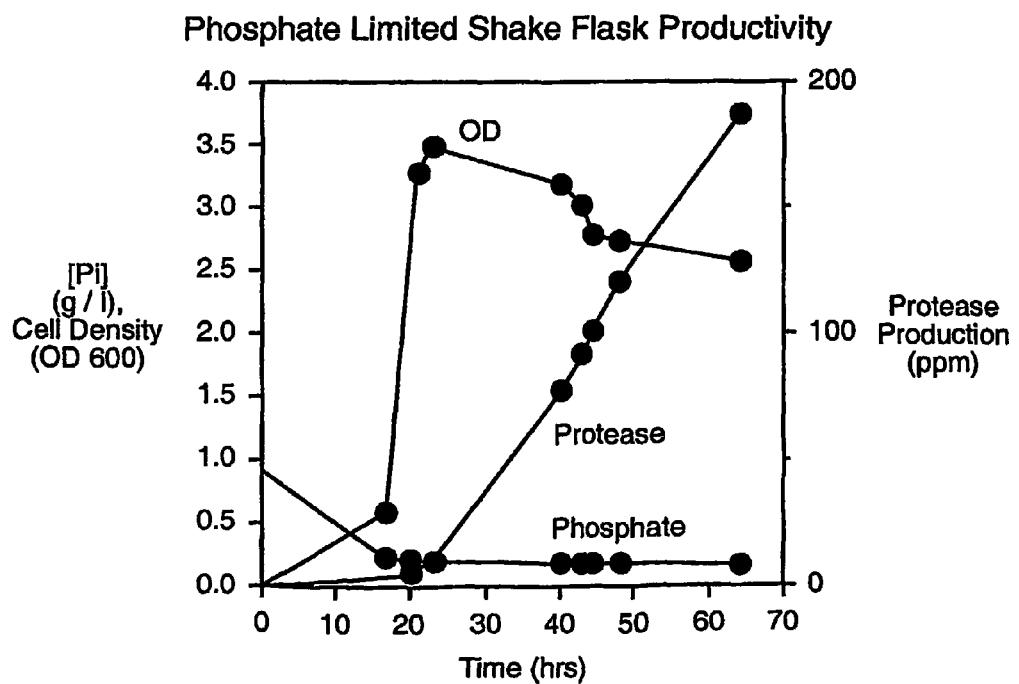
FIG._4B

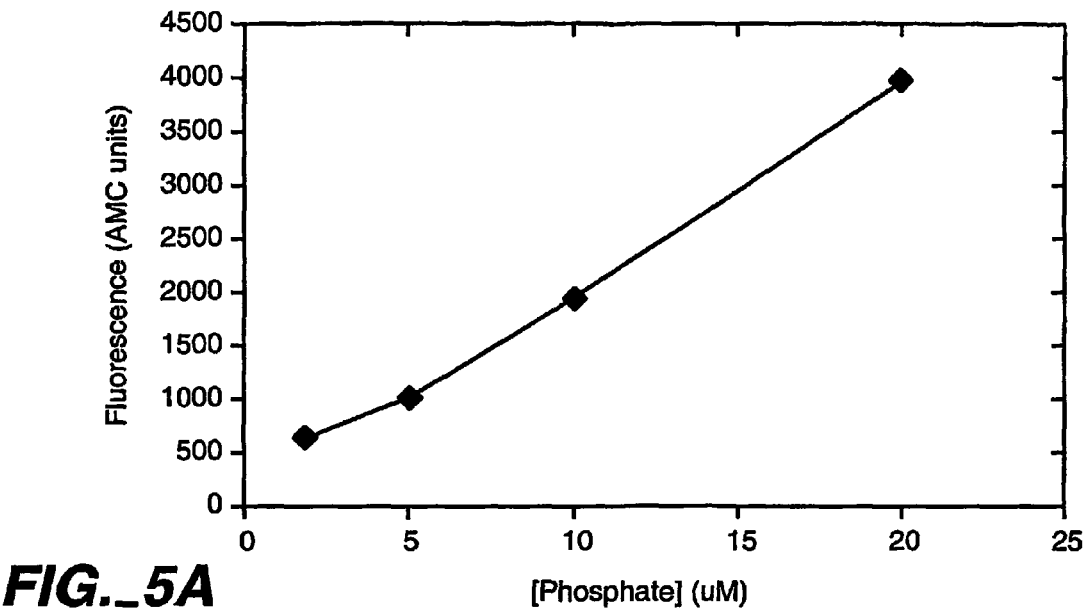
FIG._5A
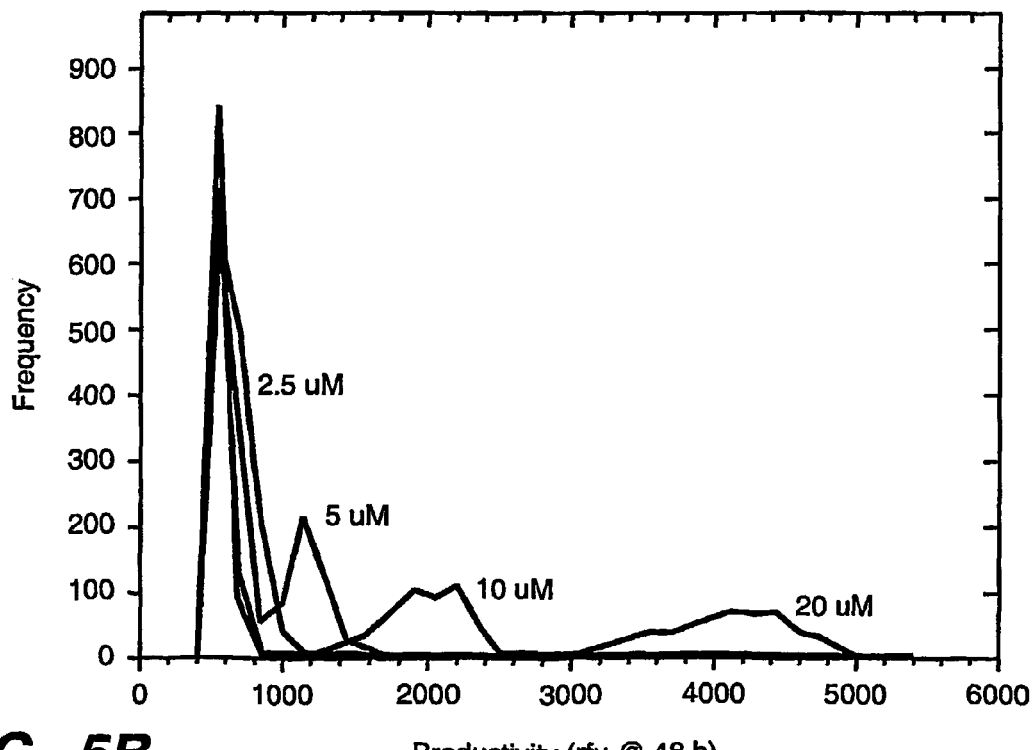
FIG._5B

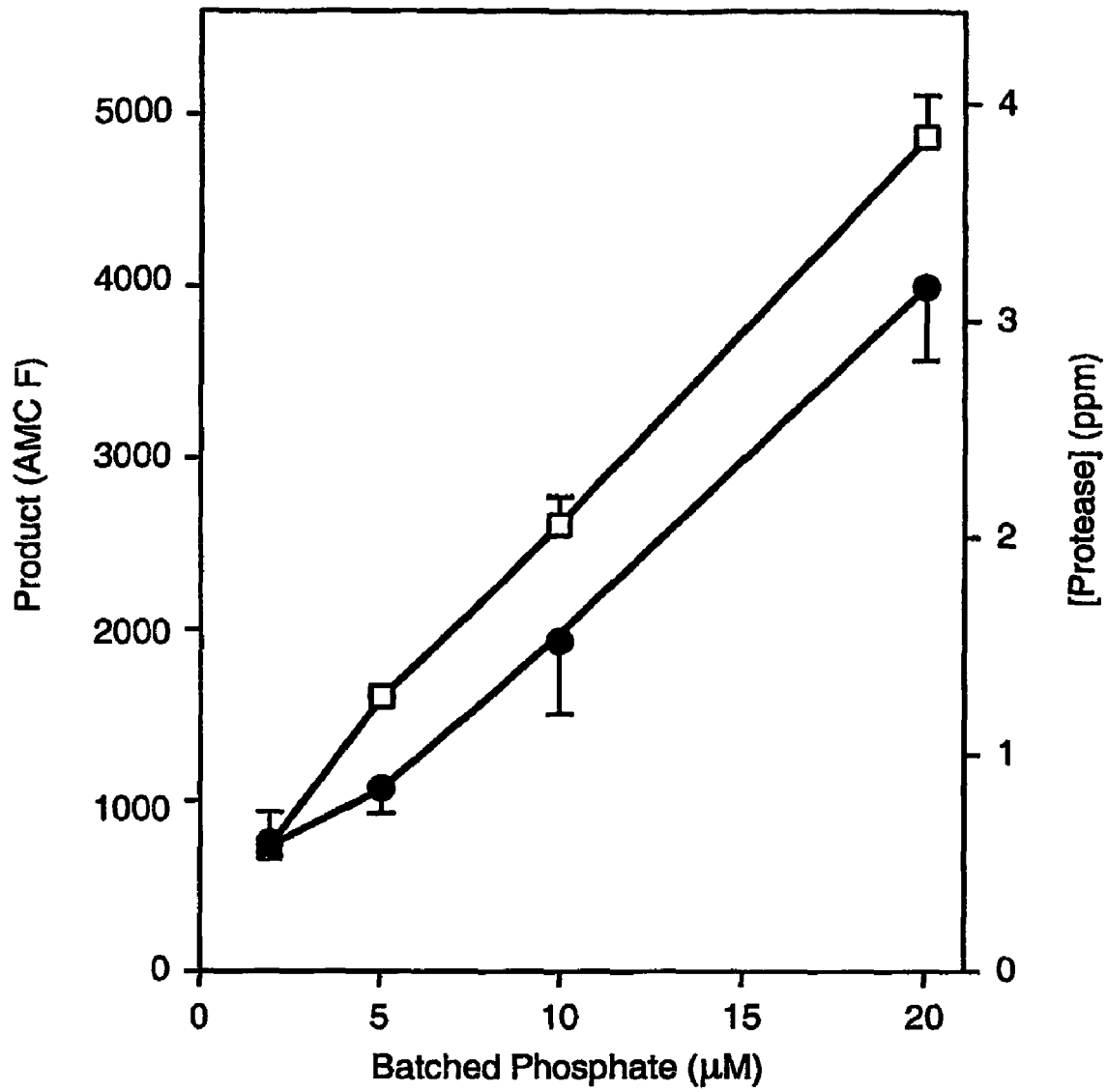
FIG._5C

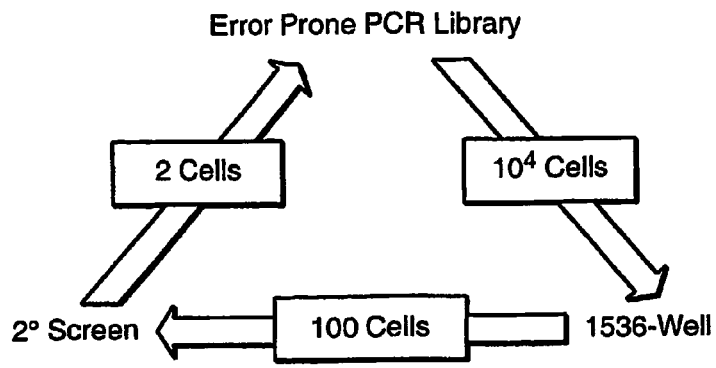
FIG._6A
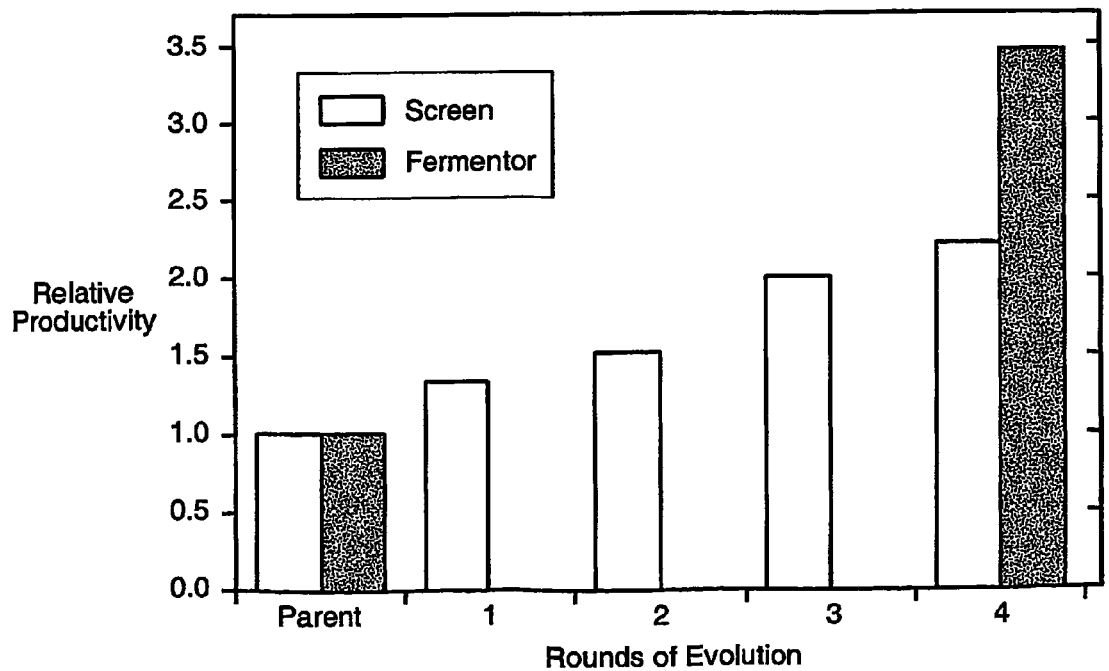
FIG._6B

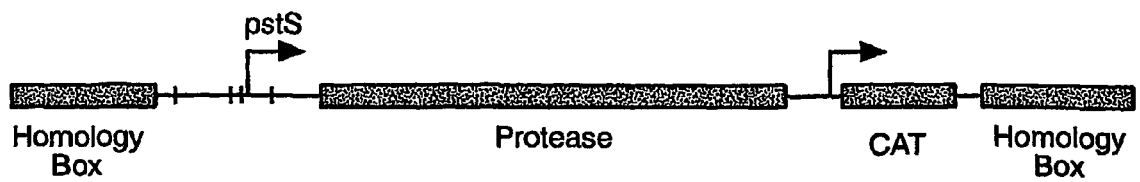
FIG._7
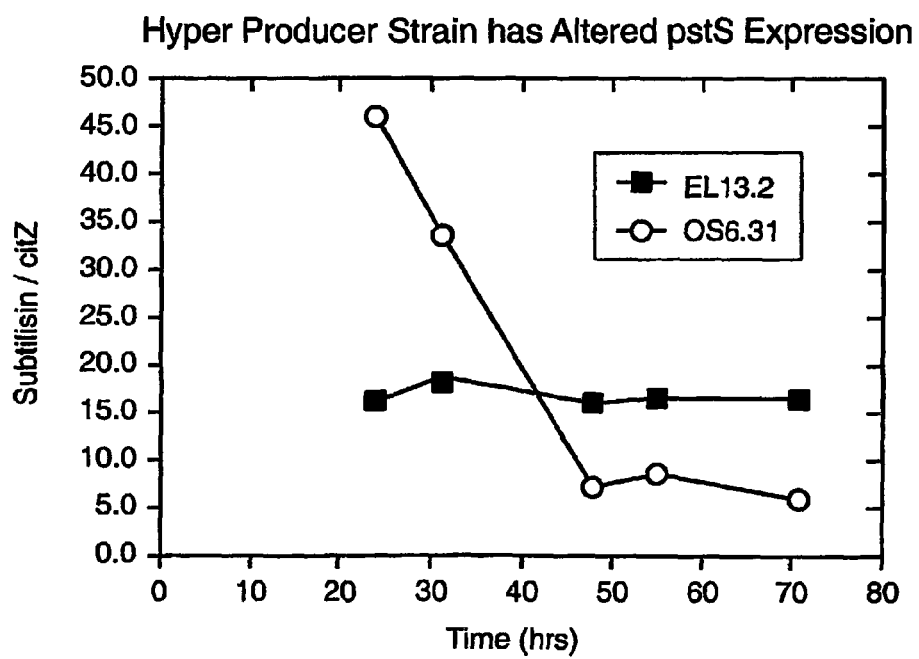
FIG._8

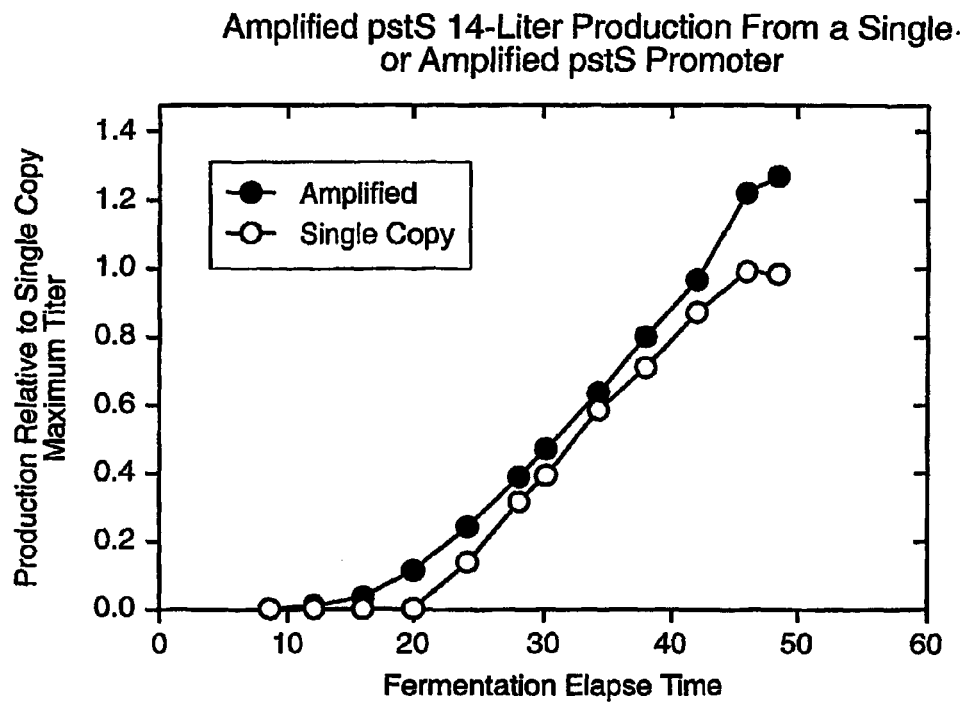
FIG._9
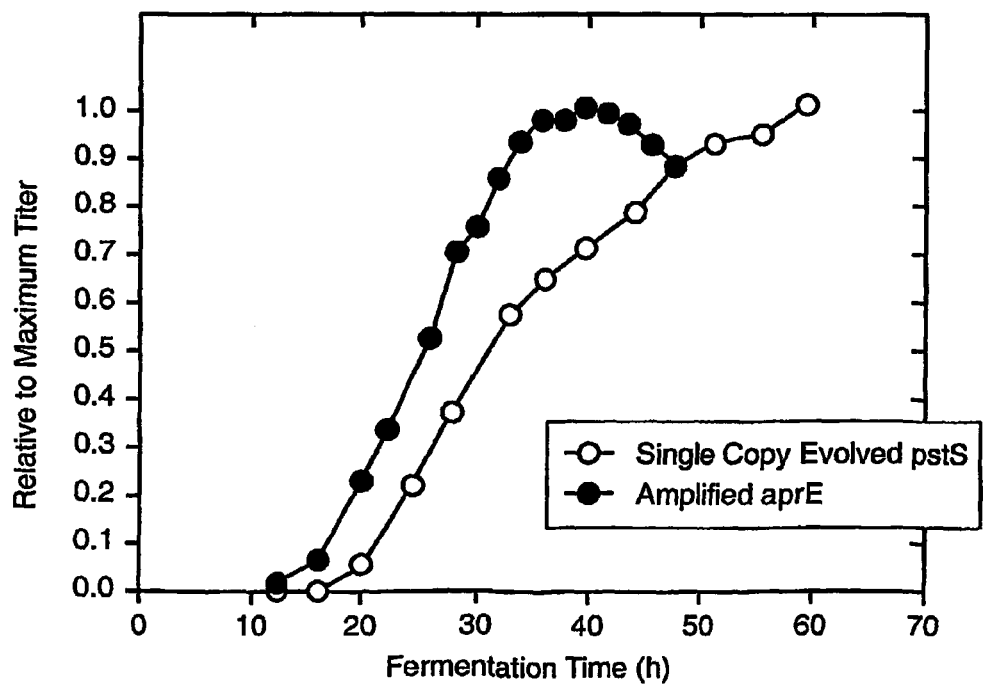
FIG._10

SEQUENCE LISTING

```
<160> NUMBER OF SEQ ID NOS: 9

<210> SEQ ID NO 1
<211> LENGTH: 39
<212> TYPE: DNA
<213> ORGANISM: Artificial Sequence
<220> FEATURE:
<223> OTHER INFORMATION: OSPS-1 primer

<400> SEQUENCE: 1
gtctttgctt ggcgaatgtt catccatgat gtgggcgtt                              39

<210> SEQ ID NO 2
<211> LENGTH: 39
<212> TYPE: DNA
<213> ORGANISM: Artificial Sequence
<220> FEATURE:
<223> OTHER INFORMATION: OSPS-4 primer

<400> SEQUENCE: 2
gacttactta aaagactatt ctgtcatgca gctgcaatc                              39

<210> SEQ ID NO 3
<211> LENGTH: 21
<212> TYPE: DNA
<213> ORGANISM: Artificial Sequence
<220> FEATURE:
<223> OTHER INFORMATION: OSFN-5 primer
```

```
<400> SEQUENCE: 3
ggcaaccccg acaggcgtaa t                                              21

<210> SEQ ID NO 4
<211> LENGTH: 24
<212> TYPE: DNA
<213> ORGANISM: Artificial Sequence
<220> FEATURE:
<223> OTHER INFORMATION: OSFN-4 primer

<400> SEQUENCE: 4
gatgaacatt cgccaagcaa agac                                           24

<210> SEQ ID NO 5
<211> LENGTH: 24
<212> TYPE: DNA
<213> ORGANISM: Artificial Sequence
<220> FEATURE:
<223> OTHER INFORMATION: OSPS-5 primer

<400> SEQUENCE: 5
acagaatagt cttttaagta agtc                                           24

<210> SEQ ID NO 6
<211> LENGTH: 30
<212> TYPE: DNA
<213> ORGANISM: Artificial Sequence
<220> FEATURE:
<223> OTHER INFORMATION: OSBS-1 primer

<400> SEQUENCE: 6
atatgtggtg ccgaaacgct ctggggtaac                                     30

<210> SEQ ID NO 7
<211> LENGTH: 30
<212> TYPE: DNA
<213> ORGANISM: Artificial Sequence
<220> FEATURE:
<223> OTHER INFORMATION: OSBS-1 primer

<400> SEQUENCE: 7
atatgtggtg ccgaaacgct ctggggtaac                                     30

<210> SEQ ID NO 8
<211> LENGTH: 30
<212> TYPE: DNA
<213> ORGANISM: Artificial Sequence
<220> FEATURE:
<223> OTHER INFORMATION: OSBS-8 primer

<400> SEQUENCE: 8
cttttcttca tgcgccgtca gcttttctc                                      30

<210> SEQ ID NO 9
<211> LENGTH: 9
<212> TYPE: DNA
<213> ORGANISM: Artificial Sequence
<220> FEATURE:
<223> OTHER INFORMATION: +1 pstS mutation position

<400> SEQUENCE: 9 gtaggacaa                                                             9
```

PHOSPHATE LIMITED INDUCIBLE PROMOTER AND A *BACILLUS* EXPRESSION SYSTEM

This application is a 371 of PCT/US02/23829 filed Jul. 26, 2002 which claims benefit to provisional application 60/308, 922 filed Jul. 30, 2001.

FIELD OF THE INVENTION

The present invention provides methods and compositions of improved *Bacillus* expression systems. In particularly preferred embodiments, the methods and compositions further comprise a phosphate-limited inducible promoter.

BACKGROUND OF THE INVENTION

One desired property for a *Bacillus* expression cassette is a strong promoter, induced in stationary phase from a single gene copy. However, it was originally believed that a single gene expression system would not deliver enough messages to saturate the expression machinery of the *Bacillus* host. Thus, the current *Bacillus* production protocols have been designed such that amplification is utilized in order to create tandem gene repeats. Two problems typically arise from the use of these repeats. First, genetic manipulation of tandem genes is very difficult. Consequently, protein engineering is performed in lab strains as single copy, then later moved from a lab strain into a production strain and amplified before testing. This causes delays in product development and is plagued by numerous concerns, including the differences between the characteristics of screen and production strains. Second, the amplification process used to make the repeats requires an antibiotic marker, which is not allowed for use in some production strains (e.g., depending upon the product produced by the strains). Thus, there is a need for improved *Bacillus* expression systems.

SUMMARY OF THE INVENTION

The present invention provides improved methods and compositions for *Bacillus* expression systems. In preferred embodiments, the present invention provides evolvable production strains of *B. subtilis* exhibiting continuous or high level expression during protein evolution. In particularly preferred embodiments, the evolved *B. subtilis* pstS promoter of the present invention facilitates screening and production of secreted proteins.

In some particularly preferred embodiments, the evolved promoter of the present invention provides better specific productivity in low phosphate medium than other stationary phase promoters (e.g., aprE), drives long term production of relatively large amounts of protein during fermentation, is not sensitive to comK, finds use as a single gene with no antibiotic marker, and finds use in production as a single or amplified gene. Furthermore, in some embodiments, the use of a sporulation minus strain (e.g., spoIIe) prevents cells from entering the non-productive spore state.

In some preferred embodiments, the present invention provides isolated nucleic acid comprising a *B. subtilis* PstS promoter variant. In some particularly preferred embodiments, the present invention provides an isolated nucleic acid that encodes OS-6. In some alternative embodiments, the present invention provides at least one *B. subtilis* host cell comprising nucleic acid comprising a *B. subtilis* PstS promoter variant. In still further embodiments, the present invention provides host cells in which the *B. subtilis* PstS promoter variant nucleic acid is integrated into the chromosome of the host cell. In yet additional embodiments, the present invention provides host cells that further comprise a nucleic acid encoding a polypeptide of interest under the transcriptional control of the PstS promoter variant.

The present invention also provides expression constructs comprising an isolated nucleic acid encoding *B. subtilis* PstS promoter and a nucleic acid molecule encoding a polypeptide of interest.

The present invention further provides methods for controlling the expression kinetics for a protein of interest, wherein preferred methods comprise culturing the cells under phosphate limiting conditions. In other embodiments, the present invention provides methods for producing a protein. In some preferred embodiments, the methods of the present invention comprise providing a host cell transformed with an expression vector comprising nucleic acid encoding at least one PstS promoter variant, cultivating the transformed host cell under conditions suitable for said host cell to produce the protein; and recovering the protein.

The present invention also provides methods for screening mutants cells for protein secretion (i.e., secretion of a protein of interest) comprising: providing a host cell transformed with an expression vector comprising PstS promoter; cultivating the transformed host cell under conditions suitable for the host cell to produce the protein in the presence of a hydrolysable substrate; and measuring the extent of hydrolysis of the substrate.

The present invention further provides *Bacillus* host cells capable of expressing a heterologous sequence under nutrient limited conditions. In some preferred embodiments, the expression by *Bacillus* is prolonged.

DESCRIPTION OF THE DRAWINGS

FIG. 1 illustrates the construction of the OS6 PstS promoter expression domain. The PstS promoter region (~400 bp) was amplified by PCR from *B. subtilis* W168 chromosomal DNA using chimeric primers with ends complementary to yhf and subtilisin flanking regions (OSPS-1 [SEQ ID NO:1] and OSPS-4 [SEQ ID NO:2]), using methods known in the art. In addition, two chromosome PCR products were generated using OS2 chromosomal DNA as template, utilizing methods known in the art and primers OSFN-5 (SEQ ID NO:3) and OSFN-4 (SEQ ID NO:4), as well as OSPS-5 (SEQ ID NO:5) and OSBS-1 (SEQ ID NO:6). Three piece PCR fusions were assembled and transformed into OS-1.1 (apr-Δ-OS 1), using methods known in the art, to produce the strain OS6. The result was a replacement of the aprE promoter of OS2 with 206 bp of the pstS promoter, corresponding to −100 to +106.

```
                                        (SEQ ID NO: 1)
OSPS-1    GTCTTTGCTTGGCGAATGTTCATCCATGATGTGGGCGTT (SEQ ID NO: 2)
OSPS-4    GACTTACTTAAAAGACTATTCTGTCATGCAGCTGCAATC (SEQ ID NO: 3)
OSFN-5    GGCAACCCCGACAGGCGTAAT (SEQ ID NO: 4)
OSFN-4    GATGAACATTCGCCAAGCAAAGAC
```

-continued

OSPS-5    ACAGAATAGTCTTTTAAGTAAGTC                    (SEQ ID NO: 5)

OSBS-1    ATATGTGGTGCCGAAACGCTCTGGGGTAAC              (SEQ ID NO: 6)

FIG. 2A shows the density of cells grown overnight with varying phosphate concentrations. FIG. 2B shows glucose concentration for a 100 μM phosphate MOPS 1 M overnight culture of OS6.31 used to inoculate MOPS 1 M in 10(open circle), 100 (open triangle), 300 (filled square) and 500 (filled triangle) μM phosphate at 500 CFU/ml. FIG. 2C shows the level of protease production by the corresponding cell cultures described in FIG. 2B. Glucose, optical density and protease productivity were monitored at the indicated times.

FIG. 3 provides an example of culture kinetics. A strain expressing an secreted enzyme via the pstS promoter was inoculated into a culture containing a fluorescent substrate. As the strain grew, it consumed phosphate, eventually depleting it and therefore halting further growth. The phosphate limitation induced expression of the enzyme, resulting in a linear build up of enzyme in the culture. In response to enzyme buildup, substrate was cleaved to form product.

FIG. 4A provides data showing the productivity differences between a parent strain and a mutated hyperproducer. Shake-flasks (250 ml), filled with 50 ml, 100 μMP Mops 1M were each inoculated with 5000 CFU/ml of OS6.31 (squares) or EL13.2 (circles). OD (circles) and subtilisin concentration (squares) were determined at the indicated time points.

FIG. 4B provides data depicting the increase in protease production under phosphate limited conditions.

FIG. 5A provides data showing substrate hydrolysis as a function of batched phosphate concentration in medium. In these experiments, four 1536-well plates containing nutrient limited medium, suc-AF-AMC substrate and the indicated phosphate concentration (2 to 20 μM were inoculated with OS6 cells. AMC fluorescent plate averages were determined for each plate at 48 h incubation 37° C. (Y-axis).

FIG. 5B is a histogram indicating the frequency of protease producers under various initial phosphate concentrations. As indicated, as the initial phosphate concentration increased, the final cell mass was found to proportionately increase.

FIG. 5C depicts the relationship between initial phosphate concentration and protease concentration (filled circles) and substrate product released (open squares). In these experiments, the substrate, sAF-AMC, was cleaved by the protease, to release the fluorescent product, AMC.

FIG. 6A provides a schematic of the screening system used during the development of the present invention.

FIG. 6B provides a graph illustrating the evolution of the pstS/subtilisin expression cassette. Parental chromosome was amplified using primers OSBS-1 (ATATGTGGTGC-CGAAACGCTCTGGGGTAAC; SEQ ID NO:7) and OSBS-8 (CTTTTCTTCATGCGCCGTCAGCTTTTTCTC; SEQ ID NO:8) and Z-TAQ™ polymerase, resulting in a mutagenized PCR product (0.2% spontaneous mutation rate). The resulting PCR products were transformed into hyper-competent *B. subtilis* for integration into the *Bacillus* chromosome by double crossover. Clones were plated into 1536-well plates containing phosphate limited medium plus a dipeptide substrate (sucAF-AMC). Following incubation, substrate hydrolysis was measured by AMC fluorescence. The light bars indicate the average AMC hydrolysis of subtilisin positive wells for the indicated screening round (approximately $10^4$ clones). Top producers were pooled and subjected to further rounds of Z-TAQ™ mutagenesis; the screening results of these successive rounds are indicated on the graph. After round 4 of directed evolution, a single winner was selected and its behavior in 14-liter measured (dark bars) was observed.

FIG. 7 provides a schematic of the various mutations (indicated by the lines within the construct) that were introduced into the promoter, signal sequence, propeptide or protein of interest (e.g., a protease). The mutations arose during sequential rounds of error prone PCR. The mutations depicted were cumulative and not the result of a single round of mutagenesis.

FIG. 8 demonstrates that the hyper-producing strain depicted has altered PstS expression.

FIG. 9 shows amplified pstS 14-liter production from a single or an amplified pstS promoter.

FIG. 10 is a graph comparing the protein production of a single copy evolved pstS promoter versus an amplified aprE promoter.

DESCRIPTION OF THE INVENTION

The present invention provides improved methods and compositions for *Bacillus* expression systems. In particularly preferred embodiments, the present invention provides evolvable production strains of *B. subtilis* exhibiting continuous and/or high level protein expression during protein evolution. The evolved *B. subtilis* pstS promoter of the present invention facilitates screening and production of secreted proteins.

In some embodiments, the present invention provides methods for generating and screening populations of mutant microorganisms, in particular *Bacillus*, the use of the pstS promoter to drive expression of a heterologous protein, and a novel production microorganism. In a preferred embodiment the microorganism is a *Bacillus* species.

All patents and publications, including all sequences disclosed within such patents and publications, referred to herein are expressly incorporated by reference.

DEFINITIONS

Unless defined otherwise herein, all technical and scientific terms used herein have the same meaning as commonly understood by one of ordinary skill in the art to which this invention belongs (See e.g., Singleton, et al., DICTIONARY OF MICROBIOLOGY AND MOLECULAR BIOLOGY, 2D ED., John Wiley and Sons, New York [1994], and Hale & Marham, THE HARPER COLLINS DICTIONARY OF BIOLOGY, Harper Perennial, NY [1991]). Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention. Accordingly, the terms defined immediately below are more fully defined by reference to the specification as a whole.

As used herein, the term "host cell" refers to a cell that has the capacity to act as a host and expression vehicle for an incoming sequence (ie., a sequence introduced into the cell), as described herein. In one embodiment, the host cell is a microorganism. In a preferred embodiment, the host cells are *Bacillus* species.

As used herein, "*Bacillus*" refers to all species, subspecies, strains and other taxonomic groups within the genus *Bacillus*, including, but not limited to *B. subtilis, B. licheniformis, B. lentus, B. brevis, B. stearothermophilus, B. alcalophilus, B. amyloliquefaciens, B. coagulans, B. circulars, B. lautus,* and *B. thuringiensis*.

As used herein, the term "DNA construct" refers to DNA that is used to introduce nucleic acid sequences into a host cell or organism. The DNA may be generated in vitro (e.g., by PCR) or any other suitable techniques. In some preferred embodiments, the DNA construct comprises a sequence of interest. The sequence of interest's nucleic acid is operably linked to a promoter. In preferred embodiments, the promoter is the pstS promoter. In some embodiments, the DNA construct further comprises at least one selectable marker. In further embodiments, the DNA construct comprises sequences homologous to the host cell chromosome. In other embodiments, the DNA construct includes non-homologous sequences (See e.g., FIG. 1).

As used herein, the term "an oligonucleotide having a nucleotide sequence encoding a gene" means a nucleic acid sequence comprising the coding region of a gene (i.e. the nucleic acid sequence which encodes a gene product). In some embodiments, the coding region is present in a cDNA form, while in other embodiments, it is present in genomic DNA or RNA form. When present in a DNA form, the oligonucleotide may be single-stranded (i.e., the sense strand) or double-stranded. In some embodiments, suitable control elements (e.g., enhancers, promoters, splice junctions, polyadenylation signals, etc.) are placed in close proximity to the coding region of the gene if needed to permit proper initiation of transcription and/or correct processing of the primary RNA transcript. Alternatively, in some embodiments, the coding region utilized in the expression vectors of the present invention contain endogenous enhancers, splice junctions, intervening sequences, polyadenylation signals, or a combination of both endogenous and exogenous control elements.

As used herein, the terms "promoter," "promoter element," and "promoter sequence," refer to a DNA sequence which is capable of controlling the transcription of the oligonucleotide sequence into mRNA when the promoter is placed at the 5' end of (i.e., precedes) an oligonucleotide sequence. Thus, a promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mnRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by different nucleic acid sequence(s) than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). At a minimum, when an isolated nucleic acid or oligonucleotide is to be utilized to express a protein the oligonucleotide contains the sense or coding strand (i.e., the oligonucleotide may be single-stranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule.

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "wild-type" refers to a gene or gene product which has the characteristics of that gene or gene product when isolated from a naturally occurring source. Typically, a wild-type gene is that which is most frequently observed in a population and is thus arbitrarily designed the "normal" or "wild-type" form of the gene. As used herein, the terms "wild-type sequence," and "wild-type gene" are used interchangeably and refer to a sequence that is native or naturally occurring in a host cell. The wild-type sequence may encode either a homologous or heterologous protein. A homologous protein is one the host cell would produce without intervention. A heterologous protein is one that the host cell would not produce but for the intervention.

In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "mutant sequence," and "mutant gene" are used interchangeably and refer to a sequence that has an alteration in at least one codon occurring in a host cell's wild-type sequence. In preferred embodiments, the expression product of the mutant sequence is a protein with an altered amino acid sequence relative to the wild-type. In some embodiments, the expression product has an altered functional capacity (e.g., enhanced enzymatic activity).

As used herein, the terms "modified sequence" and "modified genes" are used interchangeably and refer to a deletion, insertion or interruption of naturally occurring nucleic acid sequence. In some embodiments, the expression product of the modified sequence is a truncated protein (e.g., if the modification is a deletion or interruption of the sequence). In some preferred embodiments, the truncated protein retains biological activity. In alternative embodiments, the expression product of the modified sequence is an elongated protein (e.g., if the modification is an insertion into the nucleic acid sequence). In alternative embodiments, an insertion results in the production of a truncated protein as the expression product (e.g., if the insertion results in the formation of a stop codon). Thus, it is contemplated that insertions result in either a truncated protein or an elongated protein as an expression product, depending upon the character of the insertion.

In some preferred embodiments, mutant DNA sequences are generated with site saturation mutagenesis in at least one codon. In other preferred embodiments, site saturation mutagenesis is performed for two or more codons. In yet further embodiments, mutant DNA sequences have more than 40%, more than 45%, more than 50%, more than 55%, more than 60%, more than 65%, more than 70%, more than 75%, more than 80%, more than 85%, more than 90%, more than 95%, or more than 98% homology with the wild-type sequence. Alternatively, in some embodiments, mutant DNA is generated in vivo using any known mutagenic procedure (e.g., radiation). The desired DNA sequence is then isolated and used in the methods provided herein. In some embodiments, the DNA constructs are wild-type, while in other embodiments, the constructs comprise mutant or modified sequences. These sequences may be homologous or heterologous. The terms "transforming sequence" and "DNA construct" are used interchangeably herein.

As used herein, an "incoming sequence" means a DNA sequence that is newly introduced into the host cell chromosome or genome. The sequence may encode one or more proteins of interest. The incoming sequence may comprise a promoter operably linked to a sequence of interest. In some embodiments, incoming sequences comprise sequence that is already present in the genome of the cell to be transformed, while in other embodiments, it is not already present in the genome of the cell to be transformed (i.e., in some embodiments, it is homologous, while in other embodiments, it is heterologous sequence).

In some embodiments, the incoming sequence encodes at least one heterologous protein, including, but not limited to hormones, enzymes, growth factors. In some preferred embodiments, the incoming sequence encodes at least one enzyme including, but not limited to hydrolases, proteases, esterases, lipases, phenol oxidases, permeases, amylases, pullulanases, cellulases, glucose isomerases, laccases, and protein disulfide isomerases.

In an alternative embodiment, the incoming sequence encodes a functional wild-type gene or operon, a functional mutant gene or operon, or a non-functional gene or operon. In some embodiments, the non-functional sequence is inserted into a target sequence to disrupt function, thereby allowing a determination of function of the disrupted gene.

As used herein, the term "flanking sequence," refers to any sequence that is either upstream or downstream of the sequence being discussed (e.g., for genes A B C, gene B is flanked by the A and C gene sequences). In some preferred embodiments, the incoming sequence is flanked by a homology box on each side. In one more preferred embodiment, the incoming sequence and the homology boxes comprise a unit that is flanked by stuffer sequence (as defined below) on each side. While a flanking sequence may be present on only a single side (either 3' or 5'), in preferred embodiments, flanking sequences are present on each side of the sequence being flanked.

As used herein, "stuffer sequence" refers any extra DNA that flanks the homology boxes. In most cases, these are typically vector sequences. However, these sequences are contemplated to be any non-homologous DNA sequence. Indeed, a stuffer sequence provides a non-critical target for a cell to initiate DNA uptake. It is not intended that the present invention be limited to any specific mechanism or sequence.

As used herein, the term "homology box" refers to the sequences flanking a sequence of interest. In preferred embodiments, the sequence of each homology box is homologous to a sequence in the *Bacillus* chromosome. These sequences direct where in the *Bacillus* chromosome the new construct gets integrated and what part of the *Bacillus* chromosome is replaced by the incoming sequence.

As used herein, the term "homologous recombination" refers to the exchange of DNA fragments between two DNA molecules or paired chromosomes (i.e., during crossing over) at the site of identical nucleotide sequences. In a preferred embodiment, chromosomal integration is accomplished via homologous recombination.

As used herein, the term "homologous sequence" refers to a sequence that is found in the same genetic source or species as the host cell. For example, the host cell strain may be deficient in a specific gene. If that gene is found in other strains of the same species the gene would be considered a homologous sequence.

As used herein, the term "heterologous sequence" refers to a sequence derived from a different genetic source or species than the host cell. In some embodiments, a heterologous sequence is a non-host sequence, while in other embodiments, it is a modified sequence, a sequence from a different host cell strain, or a homologous sequence from a different chromosomal location of the host cell.

The term "transfection" as used herein refers to the introduction of foreign DNA into cells. Transfection may be accomplished by a variety of means known to the art including calcium phosphate-DNA co-precipitation, DEAB-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

As used herein, the term "chromosomal integration" refers to the process whereby the incoming sequence is introduced into the chromosome (i.e., genome) of a host cell. In some particularly preferred embodiments of the present invention, the incoming sequence is introduced into the *Bacillus* chromosome. In this process, the homology boxes of the transforming DNA align with homologous regions of the chromosome. Subsequently, the sequence between the homology boxes is replaced by the incoming sequence in a double crossover (i.e., homologous recombination).

As used herein, the term "selectable marker" refers to the use of any "marker" (ie., indicator), which indicates the presence or absence of a protein or gene of interest. In some embodiments, the term encompasses genes which encode an enzymatic activity that confers the ability to grow in medium lacking what would otherwise be an essential. In other embodiments, a selectable marker confers resistance to an antibiotic or drug upon the cell in which the selectable marker is expressed. In addition, selectable markers include markers (e.g., genes) that confer antibiotic resistance or a metabolic advantage to the host cell, such that cells containing exogenous DNA are distinguishable from cells that have not received any exogenous sequence during the transformation. A "residing selectable marker" is one that is located on the chromosome of the microorganism to be transformed.

"Amplification" is defined herein as the production of additional copies of a nucleic acid sequence and is generally carried out using polymerase chain reaction and other technologies that are well known in the art. As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a DNA sample (e.g., genomic DNA) without cloning or purification. The length of the amplified segment of the desired target sequence is determined by the relative positions of two oligonucleotide primers with respect to each other, and therefore, this length is a controllable parameter. Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; or incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

The Pho Network

The Pho network in *Bacillus* consists of many components and affects all cell machinery. The Pho regulon of *B. subtilis* includes the structural genes for three secreted alkaline phosphatases (Apases): phoA—expressed primarily during phosphate starvation; phoB expressed from tandem promoters either during phosphate starvation or during stage II of spore development; phoD expressed during phosphate starvation and encoding an enzyme with alkaline phosphodiesterase activity as well as APase activity. The phoD alkaline phosphatases also has a putative role in cell wall teichoic acid turnover during phosphate deprivation.

Other Pho genes include: the tuaABCDEFGH operon, which is responsible for synthesis of an anionic cell wall polymer, teichuronic acid (P-free); tagAB, tag DEF divergon, responsible for synthesis of teichoic acids (poly(glycerol phosphate)) of cell walls; pstSACB1B2 genes encoding the phosphate transport system; and the phoPR operon. In *Bacillus* genome databases, pst genes have been referred to using different names (pstS=yqgG, pstC=yqgH, pstA=yqgI, pstB1=yqgJ, pstB2=yqgk). Nonetheless, the Pho regulon offers several strong, regulated promoters, which can be used alone or in combination for phosphate regulated expression of genes of interest. The critical feature is the use of appropriate media and growth conditions to utilize the full potential of these and other inducible *Bacillus* promoters. Other useful promoters are those induced under stressful environmental conditions (ie., the induction of specific starvation responses, such as the stringent response and the general starvation response). For example, U.S. Pat. No. 6,175,060 describes the control of plant expression patterns involving a phosphate-depleted inducible promoter and phosphate limitation.

U.S. Pat. No. 5,304,472 describes the control of the extent and rate of production of *E. coli* expression by mutations in PstS such that phosphate induced promoters induce under non-starvation conditions. This Patent indicates that polypeptide transcription is driven by the phoA promoter and expression is controlled by varying the phosphate concentration in the culture medium. This Patent further indicates that phosphate starvation interferes with protein expression in *E. coli*. Unlike, *B. subtilis* which has evolved to produce proteins under phosphate limiting conditions, the *E. coli* pstS system requires non stationary production. Thus, it is contemplated that the process described in this Patent will not find use in *B. subtilis* production systems.

U.S. Pat. No. 5,789,199 suggests removing the native pstS gene from *E. coli* and using variant pstS gene products to facilitate heterologous protein production. Over-expression of DsbA or DsbC is said to facilitate disulfide arrangement. The mutations described in U.S. Pat. No. 5,789,199 and U.S. Pat. No. 5,304,472 lie in the pstS coding region and are targeted to increase pstS expression under non-phosphate limiting conditions In most embodiments of the present invention, sporulation negative mutants are preferred to sporulation competent strains. Any sporulation negative mutant may be used in the present invention. In some embodiments, a preferred sporulation negative mutant is spoIIe⁻.

Construct Assembly

In one general embodiment, the present invention involves assembling a DNA construct in vitro, followed by direct cloning of such construct into competent *Bacillus* cells, such that the construct becomes integrated into the *Bacillus* genome. For example, in some embodiments PCR fusion and/or ligation are employed to assemble a DNA construct in vitro. In a preferred embodiment, the DNA construct is a non-plasmid DNA construct. In another embodiment, the DNA construct comprises a DNA into which a mutation has been introduced. This construct is then used to transform *Bacillus* cells. In this regard, highly competent mutants of *Bacillus* are preferably employed to facilitate the direct cloning of the constructs into the cells. For example, *Bacillus* carrying the comK gene under the control of a xylose-inducible promoter (Pxyl-comK) can be reliably transformed with very high efficiency, as described herein. Any suitable method known in the art may be used to transform the cells. The DNA construct may be inserted into a vector (i.e., a plasmid), prior to transformation. In some preferred embodiments, the circular plasmid is cut using an appropriate restriction enzyme (i.e., one that does not disrupt the DNA construct). Thus, in some embodiments, circular plasmids find use with the present invention. However, in alternative embodiments, linear plasmids are used. In some embodiments, the DNA construct (i.e., the PCR product) is used without the presence of plasmid DNA.

In some preferred embodiments, libraries of mutants are generated. It is contemplated that the library of mutants be screened according to the methods provided herein. However, any appropriate method known to those skilled in the art will find use with the present invention. Generally, the inventive methods involve the isolation of various host cell cultures for the purpose of selecting higher expression and/or secretion of the protein of interest. Prior productivity screens were poor predictors of which mutants would demonstrate enhanced protein production in large scale fermentations. Thus, the present invention fulfills a need in the art for improved screening and production methods.

In a general aspect, the screening methods described herein provide fast and predictive methods for identifying clones of interest. In some embodiments, a host cell library (i.e., host cells transformed with a DNA construct) is plated at a concentration of 0.5 CFU/well in 1536-well plates with a slowly hydrolysable substrate (e.g., sAFAMC). The cells are cultured at least 48 hours to assay for robust long-term productivity. Contents from the five wells with the highest signal (e.g., fluorescence) level are assayed in a secondary screen (e.g., using sAAPFpNA), to confirm primary screen activity. The secondary screen is essential in eliminating potential false-positive results by using statistical analysis concerning large number distributions.

Cells that demonstrate enhanced productivity of the protein of interest using the screening methods provided for herein also possess enhanced protein production in large scale production methods, as well as prolonged protein secretion. The use of the nutrient limited inducible promoters provides methods of controlling expression kinetics, which are contemplated to assist in screening.

EXPERIMENTAL

The following examples are illustrative and are not intended to limit the present invention.

In the experimental disclosure which follows, the following abbreviations apply: C (degrees Centigrade); rpm (revolutions per minute); H₂O (water); aa (amino acid); bp (base pair); kb (kilobase pair); kD (kilodaltons); gm, G, and g (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); OD₆₂₀ (optical density at 620 nm); MW (molecular weight); sec (seconds); min(s)(minute/minutes); hr(s)(hour/hours); MgCl₂ (magnesium chloride); NaCl (sodium chloride); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); SDS (sodium dodecyl sulfate); Tris (tris(hydroxymethyl)aminomethane); w/v (weight to volume); v/v (volume to volume); Amersham (Amersham Pharmacia Biotech, Arlington Heights, Ill.); ICN (ICN Biomedicals, Inc., Aurora, Ohio); ATCC (American Type Culture Collection, Rockville, Md.); BioRad (BioRad, Richmond, Calif.); Clontech (CLONTECH Laboratories, Palo Alto, Calif.); GIBCO BRL or Gibco BRL (Life Technologies, Inc., Gaithersburg, Md.); Invitrogen (Invitrogen Corp., San Diego, Calif.); Kodak (Eastman Kodak Co., New Haven, Conn.); New England Biolabs (New England Biolabs, Inc., Beverly, Mass.); Novagen (Novagen, Inc., Madison, Wis.); Pharmacia (Pharmacia, Inc., Piscataway, N.J.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Qiagen (Qiagen, Valencia, Calif.); Perkin Elmer (Perkin Elmer, Wellesley, Mass.); and PE/ABI (Perkin Elmer/Applied Biosystems, Foster City, Calif.).

Example 1

Construction of OS6 PstS Promoter Expression Domain and Transformation in *Bacillus*

A fragment containing the pstS promoter was obtained by PCR using primers OSPS-1 (SEQ ID NO: 1) and OSPS-4 (SEQ ID NO:2) and chromosomal DNA from *B. subtilis* strain W168. A second fragment containing the subtilisin gene was obtained by PCR using primers OSPS-5 (SEQ ID NO:3) and OSBS-1 (SEQ ID NO:6) and OS2 chromosomal DNA. A third fragment containing upstream chromosomal sequences was obtained by PCR using primers OSFN-5 (SEQ ID NO:5) and OSFN-4 (SEQ ID NO:4) and OS2 chromosomal DNA. These fragments provided the preferred overlaps of at least 15 nucleotides for assembly. Indeed, in a majority of the experiments used in the development of the present invention, 18-20 nucleotide overlaps were used. After purification using standard methods known in the art, the fragments were fused together using methods well known in the art. The primer sequences used are shown below:

OSPS-1:   GTCTTTGCTTGGCGAATGTTCATCCATGATGTGGGCGTT   (SEQ ID NO: 1)

OSPS-4:   GACTTACTTAAAAGACTATTCTGTCATGCAGCTGCAATC   (SEQ ID NO: 2)

OSFN-5:   GGCAACCCCGACAGGCGTAAT   (SEQ ID NO: 3)

OSFN-4:   GATGAACATTCGCCAAGCAAAGAC   (SEQ ID NO: 4)

OSPS-5:   ACAGAATAGTCTTTTAAGTAAGTC   (SEQ ID NO: 5)

OSBS-1:   ATATGTGGTGCCGAAACGCTCTGGGGTAAC   (SEQ ID NO: 6)

A typical PCR reaction (100µl) contained 1X Pfu Buffer, 1.5 µl 10mM dNTPs, 1 µl 25 µM primer, 1 µl Pfu TURBO® DNA polymerase, and 200 ng plasmid DNA. The cycling conditions were: 95° C. for 35 seconds for one cycle, followed by 16 cycles of 95° C. for 35 seconds, 50° C. for 1 minute, 68° C. for 16.5 minutes. Following cycling, the reaction mixtures were held at 68° C. for 7 minutes.

The final PCR product (i.e., the DNA construct), is shown in FIG. 1. A *Bacillus* strain (OS-1.1 [apr- -OS 1]) was directly transformed with the PCR product. The transformed cells were designated "OS6." The result was a replacement of the aprE promoter of OS2 with 206 bp of the pstS promoter, corresponding to nucleotides −100 to +106.

Thus, the aprE promoter of subtilisin was replaced with the −100 to +106 region of the pstS promoter from *B. subtilis* W168 (FIG. 1). As shown in Table 1 below, the resulting strain produces subtilisin when the free phosphate in the culture becomes growth limiting.

TABLE 1

Phosphate-Limited Subtlisin Expression in OS6

| Medium | Turbidity (OD 620 nm) | Titer (mg/l subtilisin) |
| --- | --- | --- |
| Rich | 3.3 | 0 |
| Phosphate Limited | 0.11 | 13 |

Thus, in rich media, cell growth and expression are limited by oxygen or glucose, the pstS promoter remains repressed and no subtilisin is expressed because phosphate is not depleted. In contrast, under conditions where the concentration of phosphate in the medium limits growth, subtilisin expression is detected.

Example 2
Phosphate Limited Productivity

Growth under limited phosphate conditions provides uniform protein production, as described herein. FIG. 2A and 2C provide graphs showing growth (FIG. 2A) and subtilisin production (FIG. 2C) for a 100 µM phosphate MOPS 1M (see following page for Table 2, which provides the formulae used) overnight culture of OS6.31 used to inoculate MOPS 1 M in 10 (open circle), 100 (open triangle), 300 (filled square) and 500 (filled triangle) µM phosphate at 500 CFU/ml. Glucose, optical density and protease productivity were monitored at the times indicated in FIG. 2B, 2A and 2C, respectively.

As indicated in FIG. 2A, the phosphate concentration may be used to adjust stationary cell density. However, care must be taken to avoid high cell densities, because limitations on the oxygen or glucose concentrations (See, FIG. 2B) and/or medium nutrients may affect productivity. FIG. 2C depicts the loss of productivity observed at higher cell densities.

As indicated in FIG. 3, when properly adjusted, cell density and productivity remain relatively constant and predictable. The results shown in FIG. 3 were obtained from a strain expressing an secreted enzyme via the pstS promoter, which was inoculated into a culture containing a fluorescent substrate. As this strain grows, it consumes phosphate, thereby depleting the phosphate concentration in the medium, and eventually halting further growth. The phosphate limitation induces expression of the enzyme, resulting in a linear build up of enzyme in the culture. In response to enzyme buildup, the substrate is cleaved to form product.

As indicated in Table 3 below, as compared with two other stationary phase promoters, the pstS promoter provides better expression in phosphate limiting conditions.

TABLE 2

MOPS Formulae:
MOPS 1M (5 uM P, 40 mM Glucose, 250 mM Na Sulfate, 1.1 mM CaCl2, Ammonia, and metals w/o FeSO4)

| Volume or weight | Solution | Final Concentration | 10X Metals^ |
| --- | --- | --- | --- |
| 100 ml | 10X MOPS | 1 X | 25.8 G/L Na Citrate |
| 14.4 ml | 50% Glucose | 40 mM | 43.5 G/L K2SO4 |
| 10 ml | 1 M (NH$_2$)SO$_4$ | 10 mM | — |
| 0.038 ml | 0.132 M K2HPO4 | 5 uM | 1.69 G/L MnSO4*H20 |
| 1 ml | 1 M CaCl2 | 1.1 mM* | 13.2 G/L Mg SO4*7H20 |
| 60.38 gm | Na2SO4*10H2O | 187.5 mM | |
| 10.89 gm | K2SO4 | 62.5 mM | |
| 100 mls | 10 X Metals# | | |
| 0.5 ml | 10 mg/ml Chloramphenicol H20 | 5 ug/ml | |
| 100 ul | 100 mg/ml soytone | 10 ppm | |

1 liter final Volume
The pH should be adjusted to 7.3 after all components are added and dissolved
Filter sterilize 0.22 micron filter
*There is 0.1 mM CaCl2 in the 1 X MOPS
see recipes beside Table
^Based on MOPS 1 L, lower Fe reduces the absorbance in the 405 nm range, but with ammonia instead of urea

TABLE 3

Mutations that Improve Subtilisin Expression.

| Strain | 96-well[1] ppm | fermentor[2] g/l | Mutations[3] |
|---|---|---|---|
| OS6.31 | 2 | 0.6 | parent strain |
| EL13.2 | 4.4 | 2.1 | A17T, A32G, T86C, G189A [V9I], G233A, A369G (I69V), T417C, T464G, A489G (T109A) |
| EL13.3 | 4.6 | n.d. | A17T, A26G, A32G, G189A [V9I], G233A, A369G (I69V), T417C, A489G (T109A) |

[1]48 h in 10 µM phosphate MOPS 1 M medium
[2]Phosphate limited, glucose limited defined medium 14-liter fermentation
[3]Mutations are relative to +1 pstS position GTAGGACAA (SEQ ID NO: 9); changes in subtilisin signal sequence are indicated in brackets, residues changes in the mature subtilisin molecule are indicated in parentheses.

As shown in FIG. 10, under conditions where phosphate is not growth limiting, the pstS promoter drives less productivity than aprE.

Example 3

Shake Flask Productivity

Predictable stationary productivity facilitates diversity screening. FIG. 4 provides one example of a screen for detecting mutants with improved secretion and activity. A strain expressing a secreted enzyme via the pstS promoter was inoculated into a culture containing a fluorescent substrate. As the strain grew, phosphate was consumed and eventually depleted, halting further growth. The phosphate limitation induced expression of the enzyme, resulting in a linear build up of enzyme in the culture. In response to enzyme buildup, the substrate was cleaved, resulting in the production of product.

Example 4

Controlled Enzyme Productivity

The dependence of the pstS promoter on phosphate limitation provides a simple method for controlling screening kinetics. In these experiments, cells were grown overnight in MOPS 1M and then diluted to 50 cells/mL or 25,000 cells total, in 510 mL media. Cells were plated onto 1536-well microtiter plates with MOPS 1M containing SAF-AMC substrate to provide a final concentration of 7.5 µM. All plates were placed in a humidified incubator set at 37° C. and allowed to grow for 48 hours. The plates were removed and read using a Perkin Elmer HTS 7000 Plus.

FIG. 5 demonstrates the ability to adjust the AMC hydrolysis in an end point assay by altering the starting phosphate concentration in the medium. The more batched phosphate, the greater the final cell density, and the more secreted product. Controlling the batched phosphate allowed for a greater than 7-fold range of protein expression, which in turn provides additional flexibility in screen development.

Example 5

Expression Cassette Mutagenesis

As described in this Example and shown in the Figures, mutagenesis of the pstS expression cassette is useful in production of mutations that improve expression. For example, FIG. 6 depicts the 2-fold increase in expression observed through successive rounds of mutagenesis, while still maintaining phosphate regulation (Table 4).

TABLE 4

Evolved pstS Promoter Remains Phosphate Regulated

| Strain | 10 µM | 5 mM |
|---|---|---|
| Parent | 3.0 | 0.6 |
| EL13.2 | 9.4 | 1.0 |

These strains were grown overnight on LA +5 µM CMP plates, the colonies were then transferred into 100 µM phosphate MOPS medium in a 96-well plate, and incubated overnight at 37° C. with shaking, in a humidified box. Then, a 1/121 dilution of this culture was used to inoculate MOPS medium containing either 10 µM or 5 mM phosphate contained within 96-well plates. After 55 hours of incubation at 37° C. with shaking, protease activity was measured by determining the hydrolysis of Suc-AAPF-PNA by a culture sample.

To randomly mutagenize the signal sequence and propeptide of subtilisin gene, a PCR reaction using primers OSFN-5 (SEQ ID NO:3) and OSFN-4 (SEQ ID NO:4) generated the 1.9 Kb left flanking region (i.e., the yhfQ-P-O region). Primers OSPS-1 (SEQ ID NO:1) and OSPS-4 (SEQ ID NO:2) were used to mutate a 646 bp region comprising the promoter, signal sequence and propeptide region. Primers OSPS-5 (SEQ ID NO:5) and OSBS-1 (SEQ ID NO:6) were used to generate the 5.1 kb right flanking region (i.e., the yhfN-M-L region). Primers OSFN-4 (SEQ ID NO:4) and OSPS-1 (SEQ ID NO:1) and primers OSPS-4 (SEQ ID NO:4) and OSPS-5 (SEQ ID NO:5) are complementary to one another. A typical amplification reaction (100 µl) was set up using either 0.5 µM of primers OSFN-5 (SEQ ID NO:3) and OSFN-4 (SEQ ID NO:4) for the 1.9 Kb fragment, or 0.5 µM of primers OSPS-5 (SEQ ID NO:5) and OSBS-1 (SEQ ID NO:6) for the 5.1Kb fragment. To this mixture, 200 µM dNTP, 2 µl of log phase liquid culture grown to $OD_{600}$ =0.5 (source of Bacillus chromosomal DNA), 4U rTth XL polymerase, 1.25 U Pfu TURBO® DNA polymerase, 1X rTth XL polymerase buffer and 1.1 mM Mg $(OAc)_2$.

The amplification parameters for the 2.2 Kb and 3.9 Kb fragments were: 95° C. for 3 min, 95° C. for 30 sec, 54° C. for 30 sec, and 68° C. for 2 min for a total of 30 cycles.

The PCR reaction products were analyzed on an agarose gel. If the correct size fragment was observed, then the PCR product was purified using the QIAQUICK™ PCR purification kit (Qiagen), per the manufacturer's instructions.

The 646 bp fragment for mutagenizing the maturation site was amplified using Primers OSFN-4 (SEQ ID NO:4) and OSPS-4 (SEQ ID NO:2)(0.5 µM each), 33 µl 3×dNTP, 2 µl of liquid culture grown to $OD_{600}$=0.5 (ie., the source of Bacillus chromosomal DNA), 0-0.3 mM $MnCl_2$ (varies upon the rate of mutagenesis desired), 5.5 mM $MgCl_2$, 5U Taq polymerase, and 1×Taq polymerase buffer in a 100 µl reaction. The PCR amplification parameters were as follows: 95° C. for 30 sec, 54° C. for 30 sec, and 68° C. for 30 sec for a total of 30 cycles. The PCR reaction products were analyzed on an agarose gel. If the correct size fragment was seen, the PCR product was purified using the QIAquick™ PCR Purification Kit, using the kit manufacturer's instructions.

The assembly of the entire 6.8 kb fragment containing the mutagenized maturation site was done using 3-5 ul each of 646 bp, 1.9 kb, and 5.1 kb fragments, 0.5 µM each of Primers OSFN-5 (SEQ ID NO:3) and OSBS-1 (SEQ ID NO:6), 300 μM dNTP, 4U r XL polymerase, 1.25 U Pfu TURBO® DNA polymerase, 1 x rTth XL polymerase buffer, and 1.1 mM Mg (OAc)$_2$ in a 100 ul reaction. The parameters for the assembly reaction were as follows: 95° C. for 30sec, 48-50° C. for 30sec, and 68° C. for 7 min. for a total of 30 cycles. The PCR reaction products were analyzed on an agarose gel. If the correct size fragment was seen, the PCR product was transformed into Pxyl-comK *Bacillus* strains to generate a library.

Example 6

Predictive Screening Assay

Importantly, the evolved pstS promoter produces more product during 14-liter fermentation (See, FIG. 6, filled bars), demonstrating that the screen predicted production activity. Some of these mutations lie within the promoter and untranslated region of the expression cassette (See, FIG. 7). Some of the mutations lie within the pho box, a region in which phoA binds. Transcript analysis of one of the most evolved mutants (EL13.2) indicates an altered transcription pattern (See, FIG. 8).

Parental chromosome was amplified using primers OSBS-1 (SEQ ID NO:1) and OSBS-8 (SEQ ID NO:8) and Z-TAQ™ polymerase, resulting in a mutagenized PCR product (0.2% spontaneous mutation rate). The resulting PCR products were transformed into hypercompetent *B. subtilis* for integration into chromosome by double crossover. Clones were plated into 1536-well plates containing phosphate limited medium plus a dipeptide substrate (sucAF-AMC). Following incubation, substrate hydrolysis was measured by AMC fluorescence. The light bars in FIG. 6B indicate the average AMC hydrolysis of subtilisin positive wells for the indicated screening round (approximately 10$^4$ clones). Top producers were pooled and subjected to further rounds of Z-TAQ™ mutagenesis; the screening results of these successive rounds are indicated on the graph. After round 4 of directed evolution, a single winner was selected and its behavior in 14-liter measured (dark bars).

Example 7

Promoter Amplification

As shown in FIG. 9, amplification of the evolved psts promoter improves expression during fermentation. In this case, the amplification did not improve the specific productivity, but production began 4 hours earlier than with the single copy gene. An additional advantage of this promoter is that production continues longer than with amplified aprE driven expression. FIG. 10 depicts the production continuing past 60 hours whereas the aprE promoter has ceased production by 40 hours. Thus, the present invention provides means for production of the protein of interest for a prolonged period.

Although the foregoing describes a phosphate limited inducible promoter, the above techniques are suitable for use with any nutrient limited inducible promoter. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to any specific embodiments. Indeed, various modifications of the described modes for carrying out the invention which are obvious to those skilled in the art and in fields related thereto are intended to be within the scope of the following claims.

The invention claimed is:

1. An isolated nucleic acid comprising a *Bacillus subtilis* PstS promoter variant, said PstS promoter variant comprising a sequence corresponding to nucleotides −100 to +106 of PstS promoter from *B. subtilis* strain W168, wherein said sequence comprises at least one mutation chosen from A17T, A26G, A32G and T86C to provide enhanced production of a polypeptide of interest.

2. A *Bacillus subtilis* host cell comprising the nucleic acid of claim 1.

3. The host cells of claim 2, wherein said nucleic acid is integrated into the chromosome of said host cell.

4. The host cells of claim 2, further comprising a nucleic acid encoding a polypeptide of interest under the transcriptional control of said PstS promoter variant.

5. An expression construct comprising an isolated nucleic acid encoding a *B. subtilis* PstS promoter variant and a nucleic acid molecule encoding a polypeptide of interest, wherein said promoter variant comprises a sequence corresponding to nucleotides −100 to +106 of the PstS promoter from *B. subtilis* strain W168, wherein said sequence comprises at least one mutation chosen from A17T, A26G, A32G and T86C to provide enhanced production of a polypeptide of interest.

6. A *Bacillus* host cell comprising the nucleic acid of claim 1, wherein said *Bacillus* host cell expresses a heterologous sequence under nutrient limited conditions.

7. The *Bacillus* host cell of claim 6, wherein said expression is prolonged.

* * * * *